United States Patent [19]

Thayer et al.

[11] Patent Number: 5,374,743

[45] Date of Patent: Dec. 20, 1994

[54] PROCESS FOR THE SYNTHESIS OF LACTIDE OR GLYCOLIDE FROM LACTIC ACID OR GLYCOLIDE ACID OLIGOMERS

[75] Inventors: Chester A. Thayer; Harold E. Bellis, both of Wilmington, Del.

[73] Assignee: E. I. Du Pont de Nemours and Company, Wilmington, Del.

[21] Appl. No.: 128,433

[22] Filed: Sep. 30, 1993

[51] Int. Cl.$^5$ ............................................. C07D 319/00
[52] U.S. Cl. .................................................... 549/274
[58] Field of Search ........................................ 549/274

[56] References Cited

U.S. PATENT DOCUMENTS 5,023,349  6/1991  Bhatia .................................. 549/274
5,028,667  7/1991  McLain et al. ...................... 525/415
5,053,522  10/1991  Muller ................................. 549/274

*Primary Examiner*—C. Warren Ivy
*Assistant Examiner*—A. A. Owens

[57] ABSTRACT

A process for preparing lactide or glycolide from a lactic acid oligomer or glycolic acid oligomer is disclosed where the molecular weight of the synthesis reactor residue is controlled to no more than 1.2 times that in the feed. The process is carried out at 130° to 280° C. and preferably 180° to 210° C. using from 1 to 6 weight percent catalyst in the oligomer feed to the synthesis reactor. The catalysts are tin or tin compounds, yttrium or rare earth metal compounds, or antimony compounds which are known as alphahydroxycarboxylic acid cyclic dimerization or polymerization catalysts.

9 Claims, No Drawings

PROCESS FOR THE SYNTHESIS OF LACTIDE OR GLYCOLIDE FROM LACTIC ACID OR GLYCOLIDE ACID OLIGOMERS

BACKGROUND OF THE INVENTION

1. Field of the Invention

Polylactide and polyglycolide are biodegradable polymers which are manufactured commercially. The monomer used is lactide or glycolide which are cyclic dimers of lactic acid or glycolic acid and which are prepared from lactic acid or glycolic acid.

2. Prior Art

U.S. Pat. No. 5,023,349 discloses a process for the rapid conversion of oligomers of alpha-hydroxycarboxylic acids, esters or salts thereof to cyclic dimer esters in high yields by rapidly passing an inert gas through the reaction mixtures at a temperature such that the cyclic dimer is rapidly removed from the reaction mixture as it is formed. The process uses 0.1 to 1.5% and preferably 0.3 to 0.9% stannous octoate catalyst.

U.S. Pat. No. 5,053,522 discloses heating lactic acid, glycolic acid, or polylactic or polyglycolic acid of molecular weight 400 to 2,000, preferably 500 to 800, at 130° to 230° C., preferably 180° to 200° C., in the presence of 0.05 to 1.0 weight percent, preferably 0.1 to 0.8 weight percent of a tin catalyst to form lactide. The lactide formed is distilled off and additional polylactic acid is fed in continuously or batchwise.

The higher molecular weight oligomer produced by the presently used processes requires treatment to lower its molecular weight before it can be recycled to the lactide or glycolide preparation step. The need for this treatment to lower the molecular weight of the oligomer is a necessary part of the conventional lactide or glycolide production.

This high molecular weight material presents two problems. First, if the molecular weight is allowed to go too high, the viscosity increases to the point where the material becomes intractable. Second, to prevent yield loss, this high molecular weight material must be rehydrolyzed and recycled.

Dilution is a technique which can be used to control molecular weight of the oligomer remaining in the reaction mixture after cyclic dimer production. The reactions which produce cyclic dimer are uni-molecular whereas the dehydration reactions are bi-molecular. Thus the rate of dimer production is linearly proportional to oligomer concentration while dehydration is proportional to the square of the oligomer concentration. Reducing the concentration of monomer in the reactor by one half would lower the dimer production rate by one half but reduce the rate of molecular weight increase of oligomer by one half squared or one quarter. At present this is the only method known to limit the increase in molecular weight of the oligomer remaining in the reactor and this method has only marginal success. Dilution however reduces productivity and thus increases costs.

SUMMARY OF THE INVENTION

The present invention relates to an improved process for the preparation of lactide or glycolide from lactic acid oligomers or glycolic acid oligomers wherein a higher than normal amount of catalyst is used to form the cyclic dimer while preventing an increase in the molecular weight of the oligomer present.

DETAILED DESCRIPTION

In the present lactide or glycolide synthesis reactors, lactic acid oligomer chains, which generally contain about 8 to 15 lactic acid or glycolic acid residues, are catalytically cleaved to generate cyclic dimer by the reaction:

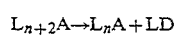

where:
- $L_{n+2}A$ is an oligomer of length $n+2$
- $L_nA$ is an oligomer of length $n$
- LD is lactide or glycolide
- "A" denotes that each oligomer terminates with an acid group.

The above reactions tend to lower the average molecular weight of the oligomer mixture in the reactor.

Simultaneously a second set of reactions involving dehydration occur:

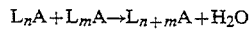

This latter reaction tends to increase the average oligomer molecular weight.

Under current process conditions, the dehydration reactions occur more rapidly than the synthesis reactions. The net effect of this competition is to increase the molecular weight of the oligomer to a degree of polymerization (DP) of 20 or more monomer units in the tails from the synthesis reactor which represents a considerable increase from the feed DP in the range of 8 to 15 monomer units in the tails.

The present invention involves the discovery that the lactide or glycolide synthesis reactions can be accelerated relative to the dehydration reactions by increasing the concentration of the catalyst. Generally the present invention provides from 1 to 8 weight percent and preferably 2 to 6 weight percent catalyst based on oligomer feed in the reactor. The result is that the molecular weight of the oligomer fed to the synthesis reactor is increased by no more than a factor of 1.2 as measured in the synthesis reactor residue. Typically the molecular weight of the feed material ranges from 400 to 2,000 and the molecular weight of the reactor residue is controlled to 480 to 2,400. Suitable catalysts include tin dust or halide or organo tin compounds of the general structure $S_n(OCR)_2$ where R is a branched or unbranched alkyl, hydroxyalkyl, or alkenyl radical having up to 18 carbon atoms or a phenyl or naphthyl radical or compounds of the general structure:

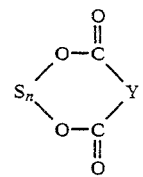

wherein Y is a branched or unbranched alkyl, hydroxyalkyl or alkenyl radical having up to 18 carbon atoms or a phenyl radical.

Examples of alkyl groups suitable for X and Y are the methyl, ethyl, n- or iso-propyl, n-, sec.- or tert.-butyl, pentyl, hexyl, heptyl or octyl radicals which, if appropriate, can contain one or more hydroxyl groups. Corresponding alkenyl radicals contain one or more double bonds. If a tin halide such as, for example, $SnCl_2$ or $SnBr_2$ is used as the catalyst, tin lactate is formed with elimination of the corresponding acid.

The preferred catalysts are tin lactate, tin tartrate, tin oxalate, tin dicaprylate, tin dilaurate, tin dipalmitate, tin distearate, tin dioleate (derivative of oleic acid), or tin naphthoate. Tin dioctoate, better described as tin-di-(2-ethylhexanoate), or tin dust are particularly preferred.

Also suitable for use as catalysts herein are the catalysts disclosed in U.S. Pat. No. 5,028,667, the disclosure of which is hereby incorporated by reference. These catalysts are compounds of yttrium and the rare earth metals of the general formula $MZ_3$ where M is yttrium or one of the rare earth metals. Rare earth metals include those elements with atomic numbers 57 through 71, namely lanthanum, cerium, praseodymium, neodymium, promethium, samarium, europium, gadolinium, terbium, dysprosium, holmium, erbium, thulium, ytterbium and lutetium. Preferred metals are yttrium, lanthanum, erbium, samarium and dysprosium. Especially preferred are yttrium, lanthanum and rare earth metals that are obtained from the mining and smelting of rare earth metal ores. In all of the catalysts the yttrium and rare earth metal is trivalent. The catalyst should preferably be at least slightly soluble in the reaction medium.

The groups bonded to the metal are denoted Z, where Z is independently chosen from $-OCR^1_3$, $-NR^1_2$, and $-CR^1_3$, wherein each $R^1$ is independently chosen from hydrogen, hydrocarbyl and substituted hydrocarbyl. It is to be understood that in the grouping $-OCR^1_3$ the carbon atom bound to the oxygen may be part of a nonaromatic carboxylic or nonaromatic heterocyclic ring formed from that carbon atom and two of the $R^1$ groups. Alternatively, one or two of the $R^1$ groups in $-CR^1_3$ may be covalently bonded to carbon, forming vinylic and acetylenic groups, respectively. Preferred Z groups contain less than 50 carbon atoms or are biologically active, provided that when a Z group is biologically active, the 50 carbon atom limit does not apply. Especially preferred Z groups include 2-ethoxyethoxy, isopropoxy, 2-phenylthioethoxy, 2-N,N-dimethylaminoethoxy, 1-methoxycarbonylethoxy, trimethylsilylmethyl, N,N-bis(trimethylsily)amino, 4-hydroxymethylbenzyloxy and the alkoxide of Vitamin $D_3$.

Antimony oxide, halide and salts of organic carboxylic acids containing up to 19 carbon atoms are also suitable for use as catalyst.

Generally the oligomer is heated from 130° to 280° C., under reduced pressure to 500 psi ($3.45 \times 10^3$ Pa), and preferably 0.01 to 1.1 atm. pressure, from 180° to 280° C., and the cyclic dimer distilled off as it is formed. The optimum temperature range depends on the cyclic dimer being produced and the pressure or vacuum, if any, applied and can be determined by simple trials.

EXAMPLES

Comparative Example

A series of experiments were run illustrating the advantages of using a higher amount of catalyst than reported in the prior art. The conditions used in these experiments are reported in Table I and the results of these experiments are reported in Table II. A batch of lactic acid oligomer with an average molecular weight of 167 was prepared from 85% aqueous lactic acid by distillation. It was analyzed by non-aqueous titration with sodium methoxide and is reported as "oligomer" in Tables I and II. The reactions were conducted in a 100 cc Parr bomb reactor (Parr Instrument Company, Moline, Ill.) constructed of Hastalloy C. The temperature was controlled externally with a Parr electrical heater. Pressure was maintained in the reactor with nitrogen at 300 psi (2,068 KPa). The reactor was stirred at approximately 100 rpm with an internal agitator.

In the oligomer plus water reactions, 85 g of oligomer plus catalyst, if used, were charged into the reactor. The reactor was closed, pressurized, and heated to 140° C. When thermal equilibrium was reached, 10 g of heated water was forced by nitrogen pressure into the reactor. The reactor was sampled immediately and repeatedly over the course of 4 hours. Each sample was analyzed by high performance liquid chromatography (HPLC) to determine the concentrations of each lactic acid oligomers and lactide, by Karl Fisher titration to determine the water content, and by non-aqueous titration to determine the total acid content. Standard computer methods were used to determine the reaction rate constants from these time evolution data.

The lactide plus oligomer reactions were conducted in a similar manner. Twenty-nine g of pure lactide was charged into the Parr reactor. The reactor was closed, pressurized, and heated to 140° C. When thermal equilibrium was reached, 58 g of heated oligomer plus catalyst, if used, was forced by nitrogen pressure into the reactor. The reactor was sampled immediately and repeatedly over the course of 4 hours. Each sample was analyzed by HPLC to determine the concentrations of each lactic acid oligomers and lactide, by Karl Fisher titration to determine the water content, and by non-aqueous titration to determine the total acid content. Standard computer methods were used to determine the reaction rate constants from these time evolution data.

The conditions used in these experiments are reported in Table I. In Tables I and II "LD" stands for lactide. In each case the reaction was run at 140° C.

TABLE I

| Run | Feed | Catalyst |
|---|---|---|
| 1 | LD + Oligomer | None |
| 2 | LD + Oligomer | 1.6% Sn (II) Octoate |
| 3 | Oligomer + $H_2O$ | None |
| 4 | Oligomer + $H_2O$ | 1.6% Sn (II) Octoate |
| 5 | Oligomer + $H_2O$ | 0.16% Sn (II) Octoate |
| 6 | LD + Oligomer | 0.16% Sn (II) Octoate |
| 7 | Oligomer | 0.53% Sn (II) Octoate |
| 8 | LD + Oligomer | 0.53% Sn (II) Octoate |
| 9 | Oligomer + $H_2O$ | 2.2% Sn (II) Octoate |
| 10 | LD + Oligomer | 2.2% Sn (II) Octoate |
| 11 | Oligomer + $H_2O$ | 4.7% Sn (II) Octoate |
| 12 | LD + Oligomer | 4.7% Sn (II) Octoate |

Table II reports the kinetic constant K for lactic acid oligomers at 140° C. as a function of Tin (II) Octoate catalyst as in run in Table I

TABLE II

| % Tin Octoate | K Dehydration (K2) L/g-mole/min | K LD Synthesis (K1) min | Ratio (K1/K2) |
|---|---|---|---|
| 0 | 0.0012 | 0.0012 | 1.0 |
| 0.16 | 0.0018 | 0.0027 | 1.5 |
| 0.53 | 0.0022 | 0.0054 | 2.5 |
| 2.2 | 0.0027 | 0.018 | 6.7 |
| 4.7 | 0.0029 | 0.038 | 13 |

As can be seen from Table II as the tin octoate concentration is increased by a factor of 9 the proportion of lactide synthesis increased by the ratio of 13/2.5 or a factor of 5.2 while the dehydration changed only slightly.

Thus by holding the catalyst concentration at a high level, the ratio of synthesis to dehydration may be controlled. In turn the molecular weight and viscosity can be kept at a low, manageable level.

EXAMPLE 1

A lactic acid oligomer was prepared by heating 2,000 g L-lactic acid with 45 g of tin(II) octoate (6%) at 180° C. using a constant nitrogen sparge at atmospheric pressure of 0.42 standard cubic feet per minute (SCFM) ($1.98 \times 10^{-4}$ m$^3$/s) over a period of 5 hours. The degree of polymerization after removing 524 g of water was 10.4.

The oligomer/catalyst mixture was fed at the rate of 5.5 g/min to a 5 tray column at 210° C. Nitrogen was fed at the base of the column at 0.67 (SCFM) ($3.16 \times 10^{-4}$ m$^3$/s) and atmospheric pressure. A total of 688 g of crude lactide were recovered overhead, of which the lactide content was 89%. Crystals from this crude analyzed 93% L-Lactide, 2% D-lactide, and 5% mesolactide. The balance of the oligomer fed was recovered as a heel with a degree of polymerization of 10.9. Thus the molecular weight had only slightly increased during the run.

EXAMPLE 2

The following experiment illustrates glycolide synthesis using 2.7% antimony oxide as the catalyst. 390 g of 70% aqueous hydroxyacetic acid (HAA) (equivalent to 273 g of HAA on a dry basis), 200 g of "Terathane", a copolymer of 1,4-butanediol having a number average molecular weight of 2000 and 14.8 g of antimony oxide (equivalent to 2.7%) were charged into a 2 liter flask. The reaction mixture was heated to 195° C. at 10 mm of mercury to remove the water.

The product which had an average oligomer length (DP) of 9.3 was then fed at a rate of 7.5g/min. to a 5 plate column over a 3.5 hour period at 255° C. using a nitrogen sparge of 0.35 SCFM ($1.65 \times 10^{-4}$ m$^3$/s) at atmospheric pressure. The product was collected in isopropyl alcohol (IPA). A wet cake was isolated by filtration and air dried. It weighed 200 g, contained 0.06% IPA and had an acidity of 0.03%. The melting point was measured on the crude and found to be 85.3° C. The yield was 50% based on the HAA fed. The heel amounted to 200 g and had a Dp of 8.4. The heel was of lower Dp than the feed and was sufficiently fluid to allow recycle.

We claim:

1. In a process for making lactides or glycolides by the catalytic depolymerization and dimerization of oligomers of lactic acid or glycolic acid to form the corresponding lactide or glycolide, the improvement comprising maintaining the ratio of the molecular weight of the residue produced during the reaction to the molecular weight of the oligomer feed to the reaction below 1.2 by carrying out the reaction at 130-280C. in the presence of 2-8% by weight cyclic dimer esterification catalyst.

2. The process of claim 1 in which the catalyst has the structure

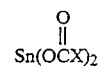

wherein X is selected from phenyl, naphthyl, and C1-18 branched or unbranched alkyl, hydroxyalkyl and alkenyl groups.

3. The process of claim 1 in which the catalyst has the structure

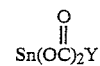

wherein Y is selected from phenyl, naphthyl, and C1-17 branched or unbranched alkyl, hydroxyalkyl and alkenyl groups.

4. The process of claim 1 wherein the process is carried out at 0.01 to 34 atmospheres.

5. The process of claim 1 wherein the process is carried out at 180° to 210° C.

6. The process of claim 1 wherein the catalyst is a tin compound.

7. The process of claim 1 wherein lactide is being produced from a lactic acid oligomer of lactic acid.

8. The process of claim 1 wherein the catalyst is tin octoate.

9. The process of claim 1 wherein the catalyst is an antimony compound which is an oxide, halide or salt of an organic carboxylic acid containing up to 19 carbon atoms.

* * * * *